United States Patent [19]
Goldowsky

[11] Patent Number: 5,360,445
[45] Date of Patent: Nov. 1, 1994

[54] BLOOD PUMP ACTUATOR

[75] Inventor: Michael Goldowsky, Valhalla, N.Y.

[73] Assignee: International Business Machines Corporation, Armonk, N.Y.

[21] Appl. No.: 788,574

[22] Filed: Nov. 6, 1991

[51] Int. Cl.$^5$ .................. A61M 1/10; A61N 1/362
[52] U.S. Cl. .................................... 623/3; 600/16
[58] Field of Search ............... 623/3; 600/16-18

[56] References Cited

U.S. PATENT DOCUMENTS 5,064,353  11/1991  Tsukahara ..................... 623/3 X

OTHER PUBLICATIONS

Designers in Action, Machine Design, Feb. 24, 1983 Cyrogenic Cooler is Almost Friction Free.
A Permanent Magnet Linear Oscillatory Motor For the Total Artificial Heart, Cheng-Huan Yang and Syed A. Nasar (U. of Kentucky).
IEEE Transactions on Biomedical Engineering, vol. BME-33, No. 3, Mar. 3, 1986–A Tubular Self-Synchronous Motor for Artificial Heart Pump.
IEEE Transactions on Biomedical Engineering, vol. 37, No. 10, Oct. 1990–On–Line Pressure Estimation for a Left Heart Assist Device.
Ferrofluidics the fluid solution (Company brochure) Apr. 1981.

Primary Examiner—Jerome L. Kruter
Assistant Examiner—Elizabeth M. Burke
Attorney, Agent, or Firm—David Aker; Ronald L. Drumheller

[57] ABSTRACT

An implantable blood pump actuator uses an efficient direct drive voice coil linear motor to power an hydraulic piston. The motor is immersed in oil and has but one moving part, a magnet which is attached to the piston. The piston is supported using a linear double acting hydrodynamic oil bearing that eliminates all wear and will potentially give an infinitely long life. There are no flexing leads, springs to break or parts to fatigue. A total artificial heart embodiment is very light, small, and as efficient as present prosthesis. The motor uses two commutated coils for high efficiency and has inherently low side forces due to the use of coils on both the inside and outside diameters of the magnet. The motor is cooled by forced convection of oil from the piston motion and by direct immersion of the coils in the oil. The highly effective cooling results in a smaller lighter weight motor.

16 Claims, 2 Drawing Sheets

BLOOD PUMP ACTUATOR

BACKGROUND OF THE INVENTION

This invention discloses the use of a direct drive linear motor that is submersed in oil and is supported on its own hydrodynamic oil bearings. All wear and metal to metal contact are eliminated. This feature is unique in the field of artificial hearts or left ventricular assist devices.

Implantable blood pumps have been worked on for several decades. These have been funded in part by the U.S. National Institutes of Health. Although much progress has been made no approach has demonstrated the high reliability needed for the actuator. Generally, the motion of a rotary electric motor is converted into the linear motion of a pusher plate to squeeze blood from rubber type ventricles. Some move on hydraulic piston which squeezes the ventricles with fluid. Some push on the ventricles directly using no hydraulics. The rotary to linear conversion mechanism such as lead screws, gear pumps and a host of other designs are prone to wear, and possess many moving parts such as the support ball bearings. These complex approaches, with many moving parts, substantially reduce the mechanical reliability attainable. Actuator approach complexity has been the major stumbling block in attaining a highly reliable, light weight prosthesis.

The proposed use of a linear direct drive like a solenoid is not new. This circumvents the rotary to linear conversion problem but no one has demonstrated a long life and efficient design. This is because most linear actuators, such as solenoids, produce large side forces and therefore require massive support bearings. Roller or ball bearings are typically used in commercial linear motors, but their use is undesireable compared to the non-wearing hydrodynamic approach of the instant invention.

Direct drive linear electric actuators have also not been used in implantable blood pumps because they have been inefficient. It is desireable to minimize the power consumed if the patient is to be truly mobile, as he is dependent on a wearable battery source. Existing linear motors are typically of the reluctance type. They are not generally efficient at the slow velocities required for ejecting blood in a direct drive. Voice coil linear motors on the other hand operate on the Lorentz force generated by a current in a coil interacting with a magnetic field. The diaphragm drive in loud speakers is an example. The loud speaker coil moves only a small amount and is attached to the diaphragm. Prior to this invention voice coil linear motors have not been used in blood pumps because they were believed to be too inefficient for the relitively long stroke and high forces required. The coil leads in loud speakers are prone to fatigue breakage. Moving coil reliability is unacceptable in a longer stroke device such as a blood pump. It is also undesireable to use conductive spring arrangements to supply the power for reliability concerns. The proposed actuator uses a moving magnet instead with a stationary coil and has no such reliability concern.

Furthermore, the proposed design uses more than one longitudinal coil to obtain a reasonably large stroke. A larger stroke reduces the force required and results in a higher linear velocity. Both effects allow a higher efficiency to be obtained. Because of the direct drive with few other losses, overall blood pump efficiency is calculated to be 20% which is as good as with present art high speed rotary motor actuators. The proposed design rivals the most efficient blood pumps to date requiring only 9 watts of power and weighs only 1.3 pounds.

The instant invention also uses coils on each side of the moving magnet unlike other voice coil designs. This reduces the side loads on the magnet and makes the use of a hydrodynamic linear oil bearing practical for supporting the moving magnet assembly.

All linear actuators need bearing support of some kind. Ball bearings are used as rollers in commercial linear motors but these pose severe space limitations if one wants to minimize the size of a blood pump. They also wear and are subject to ball indentation damage from shock loads. The proposed oil bearing is ideally suited to this application which requires the motor to run continuously. The bearing can also sustain very high shock loads without damage. This is due to the squeeze film effect in addition to the hydrodynamically generated oil film. Of equal importance, no additional moving parts are introduced by the bearing. This is very important because reliability has been a major development problem. The ball bearings used in high speed rotary motors fail prematurely, particularly when they are reversed in direction at high sped. They have to undergo billions of cycles and each cycle produces wear and fatigue.

Another advantage offered by the instant invention is one of small size and weight. The direct drive approach eliminates the need for motion conversion mechanisms which are generally larger and heavier than the high speed rotary motor used. They also reduce overall efficiency.

The highly effective forced conversion cooling of the motor using the available hydraulic fluid (oil), also distinguishes this design from voice coil designs of prior art that use ineffective air cooling (such as the loud speaker).

Having discussed the main disadvantages in the actuators used in blood pumps presently under development, such as the existence of parts that wear, low mechanical reliability, the use of many moving parts, their larger size and weight; the following objects of the instant invention can be stated.

A primary object of this invention is to eliminate all wear. This is accomplished by using a self acting linear hydrodynamic oil bearing to support a linear motor. Commercial linear motors sometimes use hydrostatic air bearings for accurate positioning requirements. These bearings are supplied with an externally supplied source of air not practical in this application. Another object of this invention is to maximize reliability by having only one moving part. This is accomplished by the synergistic use of a moving magnet linear motor with an attached hydraulic piston. The oil bearing is integral with this moving assembly. Another object is to provide a double acting hydrodynamic bearing that functions in two directions of motion. A back to back configuration accomplishes this goal where the center zone between respective halves of the bearing can communicate with ambient oil to isolate each half of the bearing. Another object of the invention is for the linear bearing to synergistically act as the hydraulic piston to pump hydraulic fluid alternately back and forth to left and right ventricles. This is accomplished by the bearing acting as both a clearance seal and a piston located between the two ventricles.

Yet another object of this invention is to provide a linear actuator that exhibits low side loads. This is accomplished by surrounding the moving magnet with drive coils at both its inner and outer diameters. The resulting large air gaps with the stator iron cause low radial instability forces because the magnet ring is kept far from the stator iron. Another object of this invention is to hydraulically couple the linear motor to a variety of blood pumping ventricles that expel blood using suitable one way valves. Another object of the instant invention is to provide very efficient liquid cooling for the linear motor. This is accomplished by submersing the entire motor in the same hydraulic fluid as used by the bearing and used to compress the ventricles. Provisions are made to cool the motor coils by direct contact with the oil and by proportioning the flow of oil over specified areas of the stator. The piston motion creates the driving force for the forces convection of oil flow. This heat is then transferred to the blood via oil convection over the ventricles. Another object of the instant invention is to produce a linear actuator that is efficient and low in weight. Some present day artificial hearts weigh upwards of two pounds where as the human heart typically weighs less than a pound. This is accomplished by utilizing, in the preferred embodiment, a double coil motor. Its stroke can be optimized and be more efficient than single coil designs used for small strokes. The forced liquid cooling of the stator by the piston also permits designing a smaller lighter weight motor.

Another object of the present invention is to provide for closed loop control of the actuator. This is accomplished by employing a position sensor to give piston position and velocity information. This sensor is also used to switch the motor coils for commutation. Yet another object of the invention is to provide a control to maintain stable location of the ventricles. The hydraulic fluid will preferentially tend to leak past the piston from left to right due to the higher pumping pressure at the left ventricle. Hence both ventricles will tend to drift toward the right side. A ventricle position sensor is used to correct the position of the ventricles.

These and other objects of the present invention are accomplished in accordance with a preferred embodiment. For illustrative purposes only, a linear motor is positioned between right and left blood pumping ventricles. A radially magnetized magnet ring is positioned inside the motor and is the only moving element of the actuator. Its radial flux passes into a surrounding stationary ferromagnetic return shell after first passing radially through coils positioned on the inside and outside of the magnet ring. The return shell or stator recirculates the flux back to the magnet. Sufficiently large air gaps separate the magnet from the coils so that no wear or contact occurs at these locations.

A piston or hyraulic pusher plate is attached to the magnet. The piston is as long as practicable to act as a support bearing. A set of double acting tapers or steps are located on its surface to generate the hydrodynamic oil film. This film separates the sliding surfaces and eliminates all wear for indefinitely long life. The bearing also serves as a piston clearance seal to alternately pump hydraulic fluid to each ventricle. The oil flow is forced to go over the motor surfaces thereby providing very efficient forced convection cooling. This allows the motor to be of minimum weight.

An annular groove located at one end of the bearing housing, is used to provide reverse leakage past the bearing when the port is intentionally overlapped by a hole in the piston. This port than functions like a valve. It allows one to compensate for long term preferential leakage past the bearing by permitting hydraulic fluid to leak back from right to left. A ventricle position sensor is used to determine when correction is needed.

The motor is cooled by oil, forced to flow by the motion of the piston, over the outside of its housing. Exit holes are provided in the housing for the oil. The movement of the magnet ring also pumps oil in and out of the confined space at the coils. Holes are provided for this flow to exit to the ventricles. A central hole in the stator also circulates oil driven by the piston. An optional nonmagnetic plug can limit or proportion this flow if desired. By proportioning the sizes of the oil exit holes the cooling flow can be optimally proportioned in areas of the motor to optimize heat extraction.

The piston bearing effectively separates the blood pump into left and right halves so that its reciprocating action alternately pressurizes the two ventricles. The ventricles may be of commonly accepted construction using seamless polyurethane compliant sacks. The inner surface of the sacks generally designated 36 is in contact with the oil while their outer surfaces 37 contact a supporting structure 27. One inlet and one outlet valve is used in each ventricle to achieve unidirectional pumping action. The proposed actuator concept can be applied to an endless variety of ventricle materials and shapes. A compliance chamber is not required for proper operation as the mechanism runs at constant internal volume.

BRIEF DESCRIPTION OF THE DRAWINGS

A brief description is now made with reference to the following figures.

DETAILED DESCRIPTION OF THE DRAWINGS

Figure 1:
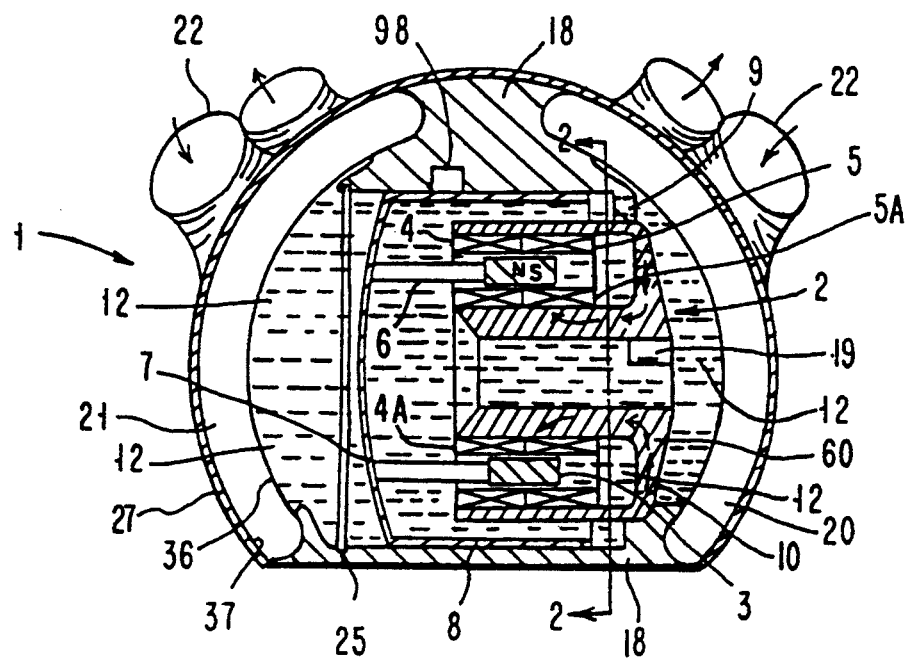
FIG. 1 is a longitudinal section through a total artificial heart blood pump. It shows the preferred embodiment voice coil, linear motor in section with the attached piston and hydrodynamic bearing. The hemispherical shaped ventricles are shown at the right and left. The housing not only supports the motor but its inner bore is part of the piston bearing.

Referring to the drawings, FIG. 1 shows the essential features of a total artificial heart implantable blood pump generally designated 1. It incorporates a voice coil type linear motor generally designated 2. The same motor concept can be applied to left ventricular assist devices or externally operated blood pumps used in open heart surgery.

Figure 2:
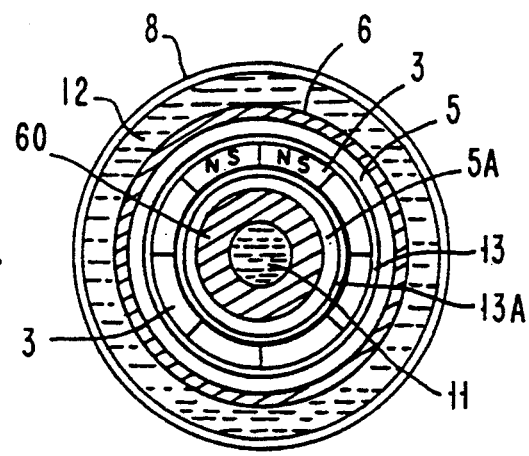
FIG. 2 is a transverse section 2—2 of FIG. 1 through the motor. It shows the round magnet ring and surrounding round coils with air gaps.

The magnet ring 3 is radially magnetized and may be fabricated of pie sliced sections of magnets in order to utilize the latest rare earth or neodymium iron boron magnet materials. These magnets are shown in FIG. 2. The magnet ring is bonded to yoke 6 which is part of piston 7. The piston may have a curved shape to resist buckling under a typical load of 150 mmhg yet with minimal weight. Integral with the piston and located at its diameter is the hydrodynamic support bearing generally designated 8. It maintains a small radial clearance with the housing which is shown enlarged in FIG. 3. Oil 12 is everywhere on the inside of the housing 18 which is generally made of non-magnetic material such as titanium to be compatible with body fluids. The bearing radial clearance is on the order of 0.001 inch and keeps the piston well centered. The magnet ring clearances with the coils are 13 and 13A respectively, with the outer and inner coils. The outer coils are 4 and 5 while the inner coils are 4A and 5A. These clearances are substantially larger than the bearing clearance to eliminate the potential for physical contact.

The motor stator 60 is high saturation iron such as permendure to minimize its weight. It serves to rout the magnet flux back to the magnet. Other flux routing geometries are also possible so this preferred embodiment is not to be limiting. The flux path is designated by the arrows shown. When the magnet is between coils 4 and 4A these coils are energized to force the magnet ring to the left. Reversing the current reverses the direction of the force. With the magnet moving to the left coils 4 and 4A are shut off when the magnet becomes positioned under coils 5 and 5A. Coils 5 and 5A are then energized. In prior-art voice coil motors one long coil might be employed to achieve a given stroke, such that the magnet is always positioned in line with a coil. Power is then wasted in turns of the coil that are not in the field of magnet. Coil turns without radial magnetic flux produce no axial force and are inefficient. This two coil design is about 30% more efficient using the same magnet ring and coil length of a one coil design. Using for example three axial coils of the same total longitudinal length is possible but gives diminishing returns in efficiency and may not be desireable. In the preferred embodiment shown the magnet length is shorter than the coil length as this gives maximum efficiency and a minimum weight stator using a two coil design. A position sensor 98 is used to monitor piston stroke and position. Reflective photo-diodes may be employed with a photocell detector which is capable of sensing grooves cut into the surface of bearing 8. As a groove passes beneath the diode's light beam, a pulse will result at the photocell. Counting the number of pulses gives absolute position and the time interval between pulses gives piston velocity. This type of digital sensor will remain drift free indefinitely as opposed to an analog sensor. Other types of sensors may also be employed such as magneto-resistors. The position and velocity signals can be used to perform closed loop control of motor position and speed.

It has been simulated that by utilizing a fast systole time on the order of 300 msec for the left ventricle (Where most of the motor power is required), that the motor efficiency is improved due to the higher velocity. This leaves more time, about 600 msec for diastole (left ventricle filling) which is beneficial. The total stroke period is typically 1,000 msec or one cycle per second to mimic the human hearts. The higher efficiency of a fast systole results in a smaller size motor. A faster systole also mimics the expulsion of blood in the human heart into the aorta (by the left ventricle).

Assume now that the piston is moving toward the right. The heart's right ventricle 21 is allowed to fill with blood while the left ventricle 20 is compressed by the oil and expells blood. The piston motion to the right forces oil through holes 9 in the housing 18. This oil first flowed over the outside of the motor 2 which received heat from the coils by conduction. Oil is also forced through holes 10 in the iron stator 60 by the pumping action of the magnet ring even though some oil leaks past the clearances 13 and 13A. This flow introduces fresh oil to the inside surfaces of the coils for direct cooling of the windings. Oil is also forced by the piston through stator center hole 11. This is a motor lightening hole whose cross sectional area is not needed to pass magnetic flux. The size of holes 9, 10, and 11 can be optimized for partitioning of the three oil flows. Oil direction is reversed through these holes when the motor reverses. Heated oil transfers its heat to the housing and to the ventricles for dissipation to the blood.

A thin rigid housing wall 27 is used as a ventricle support in order for the oil to squeeze the ventricles during systole. This wall is penetrated by artificial atria generally designated 22 which houses two one way check valves associated with each ventricle. Flow of blood in or out of the atria is shown by arrows.

Figures 3A, 3B:
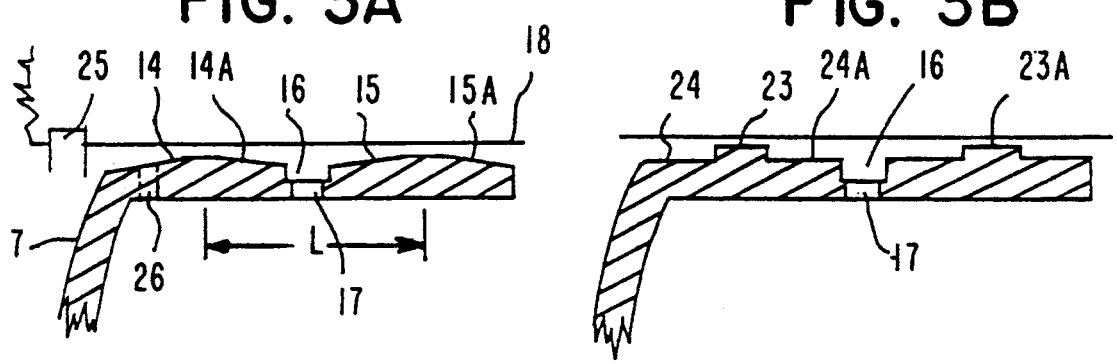
FIG. 3A is an enlarged view of FIG. 1 showing the cross sectional shape of a preferred double acting hydrodynamic bearing that has tapered surfaces.
FIG. 3B is an alternate design that employs steps instead of tapers.

FIG. 3A shows an enlarged view of the preferred bearing B. Tapered surfaces 14 and 14A are on the left and constitute the left half of the hydrodynamic bearing. Surfaces 15 and 15A compose the right half. A groove 16 is located all around the circumference and separates the two bearing halves. A plurality of radial holes 17 communicates the groove to ambient oil which exists below the surface. This groove supplies ambient oil pressure between the bearing halves forcing each half to be hydrodynamically independent. The bearing pitch L gives lateral stability to the bearing and allows it to carry a moment. With the piston moving to the left, wedge surfaces 14 and 15 generate supporting oil pressure. When moving to the right wedges 14A and 15A are active. The radial gap ratio of the taper should be about 2 to 1 to maximize load capacity. For a 2.5 inch diameter bearing, 1.5 inches long a load capacity of 10 pounds is calculated using light oil at a typical speed of 1.0 in/sec. This capacity is more than sufficient to support the radial instability forces calculated for the proposed motor. In addition to this load capacity, when the piston is stopped and reversed at the end of its stroke (about 0.8 inch), the bearing's squeeze film capability continues to keep it centered. Calculations show that about one minute would be required to squeeze out all of the oil. The motor of course never stops for more than a fraction of a second when reversing. No contact or wear will occur at any time. This squeeze film effect also allows the actuator to absorb large shock loads that would destroy ball bearings.

Another advantage of this oil bearing is its high efficiency. Only a few milliwatts of power are dissipated which is negligible.

FIG. 3B shows an alternate bearing geometry which is easier to manufacture. Raised lands 23 and 23A are used in place of tapered surfaces. A raised land with valleys 24 and 24A on either side act hydrodynamically similar to tapers 14 and 14A to generate the oil pressure.

FIG. 3A shows a circumferential groove 25 in the surface of the bore of housing 18 located near the right ventricle. The piston stroke normally does not allow hole 26 to reach groove 25. If ventricle position sensor 19 determines that ventricle 20 has drifted from an allowed maximum position (which can be due to unequal leakage past the piston), then the piston stroke is increased to overlap the groove. This permits back leakage of oil through hole 26. This leakage is only one way from the right side back to the left as right side pressure is higher during this part of the stroke. The hole basically acts as a sliding valve that is momentarily actuated by the piston. When the ventricle position is stabilized the stroke is again returned to normal. An annular groove 25 is used, instead of for example, a slot, so that hole 26 will always be properly located relative to it if the piston should rotate. Use of a groove eliminates the need to orient the piston and it may freely rotate in the bore.

This leakage compensation feature is needed because pumping against typically 125 mmhg at the left ventricle 20 will cause somewhat greater piston bearing leakage than when pumping out the right ventricle 21 which requires only 25 mmhg. If compensation were not made all of the oil would eventually be transferred to the right side.

The position sensor 19 may be similar to sensor 98. A reflective optical beam is very effective operating in oil to monitor the ventricle. These sensors are very small and reliable. Other types of sensors may be employed to provide the function desired. It should be stated that the sensor may monitor either ventricle 20 or 21 position as they would both move out of position together due to the incompressibility of the oil.

Although a preferred embodiment voice coil linear motor is disclosed, this is not intended to be limiting. For example, a single coil can be used with the magnet length longer than or equal to the coil length. Also, the disclosed double acting linear bearing can be used to support other type linear actuators as opposed to voice coil motors, in hydraulically driven blood pumps, provided the bearing's load capacity is sufficient. A large diameter bearing is chosen in the preferred embodiment to provide high load capability and therefore high reliability, using minimum viscosity oil. Low viscosity oil minimizes oil churning losses in the pump.

Other bearing locations are also possible. For example, the surface of the magnet within the coils may be employed with the coil surface acting as the housing of the bearing. Doing this however, restricts the magnet diameter to be the piston diameter unless a separate piston is used.

Figure 4:
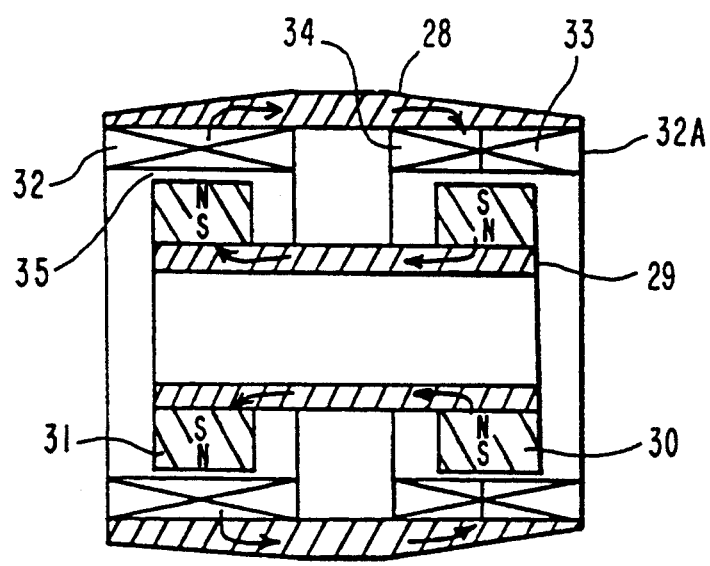
FIG. 4 is an alternate design voice coil linear motor that also exhibits very small radial side loads and hence is suitable for hydrodynamic bearing suspension. It is shown in longitudinal section being round in cross section.

FIG. 4 is an alternate design voice coil linear motor also possessing small radial side forces. The low side force is due to the large coil air gap between the magnet rings 30 and 31 with the stationary iron stator 28. A radial magnetic field is generated in the coils 32 and 32A by the radially magnetised magnet rings being in series. Ring 30 is magnetised north to south radially while ring 31 is magnetised from south to north as shown. The iron armature 29 recirculates the series flux between the magnets and is bonded to the magnets. The magnet rings and attached armature assembly are the only moving element. Single coils 32 and 32A may be used in which case the direction of current in the coils must be opposite from one another for their forces to add. A generous air gap 35 eliminates magnet contact with the coil. The piston yoke 6 is to be attached to the armature.

Each coil may be divided up into 2 smaller coils as was done in the preferred embodiment of FIG. 1. This provides a higher efficiency as previously explained. An example of this is depicted by coils 33 and 34 in place of coil 32A. Similarly, coil 32 would be replaced with two coils.

What is claimed:

1. A blood pump for use with a ventricle which receives blood, comprising a direct drive actuator for positioning proximate said ventricle, a magnet positioned inside said actuator, a stationary coil means circumferentially surrounding said magnet and spaced therefrom sufficiently so that wear and contact are minimized, a piston means attached to said magnet for pumping said ventricle, a bearing for supporting said piston means, a housing for said actuator filled with hydraulic fluid for providing cooling for said actuator, said piston means having a generally cylindrical surface having two sets of opposed taper means, a first of said sets being separated from a second of said sets by a groove, and communication means for receiving hydraulic fluid in said groove, whereby contact between said piston means and said housing is substantially eliminated.

2. The invention according to claim 1 wherein said actuator is a voice coil linear motor.

3. The invention according to claim 1 wherein said coil means includes a single coil surrounding said magnet on its outside diameter to minimize radial side forces.

4. The invention according to claim 1 wherein said coil means includes two adjacent coils, each capable of independent actuation.

5. The invention according to claim 1 wherein said piston means displaces fluid for cooling said actuator.

6. The invention according to claim 1 wherein a position sensor is provided and an average position of said ventricle is monitored by said sensor, said position changing by increasing movement of said piston means in a preset direction and wherein the bearing defines a sliding port means which is uncovered to allow leakage of said fluid across said piston means when said movement is increased.

7. The invention according to claim 1 wherein a position sensor means is provided for closed loop control of said actuator position and velocity.

8. The invention according to claim 1 wherein said housing is formed of a biocompatible material.

9. The invention according to claim 8 wherein said blood pump is implantable.

10. A blood pump for use with a ventricle which receives blood, comprising a direct drive actuator for positioning proximate said ventricle, a magnet positioned inside said actuator, a stationary coil means circumferentially surrounding said magnet and spaced therefrom sufficiently so that wear and contact are minimized, a piston means attached to said magnet for pumping said ventricle, a bearing for supporting said piston means, a housing for said actuator filled with hydraulic fluid for providing cooling for said actuator, said piston means having a generally cylindrical surface having two sets of raised steps, with lands on each side thereof, to function as a bearing.

11. The invention according to claim 10 wherein said housing is formed of a biocompatible material.

12. The invention according to claim 11 wherein said blood pump is implantable.

13. A blood pump for use with a ventricle which receives blood, comprising a direct drive actuator for positioning proximate said ventricle, a magnet positioned inside said actuator, a stationary coil means circumferentially surrounding said magnet and spaced therefrom sufficiently so that wear and contact are minimized, a piston means attached to said magnet for pumping said ventricle, a bearing for supporting said piston means, a housing for said actuator filled with hydraulic fluid for providing cooling for said actuator, ventricle sacks for said ventricle, said fluid being displaced by said piston means to alternately compress and expand said sacks, respectively located on each side of said piston means, and valve means for said sacks for controlling inflow and outflow of unidirectionally pumped blood, wherein said piston means defines a hydrodynamic bearing surface and a clearance seal, causing said fluid to be displaced on each side of said piston means.

14. The invention according to claim 13 wherein said housing is formed of a biocompatible material.

15. The invention according to claim 14 wherein said blood pump is implantable.

16. A blood pump for pumping a ventricle which receives blood through an intake one-way valve and expels blood through an exhaust one-way valve, comprising:

a piston for cyclically compressing said ventricle;

a hydraulic bearing for supporting said piston for reciprocating movement; and a linear electric motor attached to said piston for cyclically driving said piston, said linear electric motor comprising:

a radially magnetized ring axially attached to said piston;

stationary inner and outer circumferentially wound coils coaxially surrounding said magnetized ring inside and outside so as to produce an axial force on said magnetized ring when electrically energized;

a stationary stator providing a path for magnetic flux between a circumferential position radially outside of said magnetized ring and an axial position radially inside of said magnetized ring, said inner and outer coils being positioned between said stator and said magnetized ring; and a housing for said stator, magnetized ring and inner and outer coils, said housing being filled with hydraulic fluid for cooling and lubricating said linear motor.

* * * * *